United States Patent [19]

Prieels et al.

[11] Patent Number: 5,750,110
[45] Date of Patent: May 12, 1998

[54] VACCINE COMPOSITION CONTAINING ADJUVANTS

[75] Inventors: John Paul Prieels, Brussels; Nathalie Marie-Josephe Claude Garcon-Johnson, Wavre; Moncef Slaoui; Pietro Pala, both of Rixensart, all of Belgium

[73] Assignee: SmithKline Beecham Biologicals, s.a., England

[21] Appl. No.: 356,372

[22] PCT Filed: Jun. 15, 1993

[86] PCT No.: PCT/EP93/01524

§ 371 Date: Feb. 17, 1995

§ 102(e) Date: Feb. 17, 1995

[87] PCT Pub. No.: WO94/00153

PCT Pub. Date: Jan. 6, 1994

[30] Foreign Application Priority Data

Jun. 25, 1992 [GB] United Kingdom ............ 9213559
Dec. 17, 1992 [GB] United Kingdom ............ 9226283
Mar. 1, 1993 [GB] United Kingdom ............ 9304056

[51] Int. Cl.$^6$ .................. A61K 39/00; A61K 39/21; A61K 39/38
[52] U.S. Cl. ................. 424/208.1; 424/184.1; 424/188.1; 424/204.1
[58] Field of Search ............... 424/184.1, 188.1, 424/204.1, 208.1

[56] References Cited

U.S. PATENT DOCUMENTS 4,877,611 10/1989 Cantrell .................... 424/88
4,912,094 3/1990 Myers et al. .
5,057,540 10/1991 Kensil et al. ............... 514/25

OTHER PUBLICATIONS

Allison, et al., "Immunological Adjuvants and Their Mode of Action", *Biotechnology* 20, pp. 431–449 (1992).

Roberts, et al., "Active Immunization of Beef Heifers Against Luteinizing Hormone . . . " *J. Animal Science*, 68, pp.:3742–3746 (1990).

Butini, et al, 1994, "Comparitive Analysis of . . . " J. Cell Biochem. Suppl. 18B, Abstract J306.

Cohen, 1993, "Jitters Jeopardize AIDS . . . " Science 262:980–981.

Long, et al. 1984, "Glycoprotein D protects M16 . . . " Infection and Immunity 37(2):761–764.

Schneerson, et al. 1991, "Evaluation of mono . . . " J. Immunol. 147(7):2136–2140.

Weiss, et al. 1988, "CD8+T cells . . . are . . . " PNAS 85:573–576.

Schofield, et al. 1987, "r Interferon CD8+ T Cells . . . " Nature 330:664–666.

*Primary Examiner*—Lynette F. Smith
*Attorney, Agent, or Firm*—Zoltan Kerekes; Edward T. Lentz; Stephen Venetianer

[57] ABSTRACT

The present invention provides vaccine compositions comprising 3 De-O-acylated monophosphoryl lipid A and QS21. The vaccines compositions are potent inducers of CTL and γ IFN responses.

26 Claims, No Drawings

VACCINE COMPOSITION CONTAINING ADJUVANTS

The present invention relates to novel vaccine formulations, to methods for their production and to their use in medicine. In particular, the present invention relates to vaccines containing QS21, an Hplc purified non-toxic fraction derived from the bark of *Quillaja Saponaria Molina*, and 3 De-O-acylated monophosphoryl lipid A (3 D-MPL).

3 De-O-acylated monophosphoryl lipid A is known from GB2220 211 (Ribi). Chemically it is a mixture of 3-deacylated monophosphoryl lipid A with 4, 5 or 6 acylated chains and is manufactured by Ribi Immunochem Montana.

QS21 is a Hplc purified non-toxic fraction of a saponin from the bark of the South American tree *Quillaja saponaria molina* and a method for its production is disclosed (as QA21) in U.S. Pat. No. 5,057,540.

The present invention is based on the surprising discovery that formulations containing combinations of QS21 and 3 D-MPL synergistically enhance immune responses to a given antigen.

For example, a vaccine formulation of the malarial antigen, RTS, S in combination with 3D-MPL and QS21 results in a powerful synergistic induction of CS protein-specific cytotoxic T lymphocyte (CTL) response in the spleen.

RTS is a hybrid protein comprising substantially all the C-terminal portion of the circumsporozoite (CS) protein of *P. falciparum* linked, via four amino acids of the preS$_2$ portion of Hepatitis B surface antigen, to the surface (S) antigen of hepatitis B virus. Its full structure is disclosed in co-pending International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS.S.

The observation that it is possible to induce strong cytolytic T lymphocyte responses is significant as these responses, have been shown to induce protection against disease in certain animal models.

The present inventors have shown that the combination of the two adjuvants QS21 and 3D-MPL with the recombinant particulate antigen RTS.S results in a powerful induction of CS protein-specific CTL in the spleen. QS21 also enhances induction of CTL on its own, while 3D-MPL does not. The combination can be said to act in a synergistic way, because it has an effect that is larger than the sum of the separate effects of each adjuvant. The synergy between these two adjuvants for CTL induction is a surprising observation which has important implications for the use of recombinant molecules as vaccines for induction of CTL-mediated immunity.

Induction of CTL is easily seen when the target antigen is synthesised intracellularly (e.g. in infections by viruses, intracellular bacteria, or in tumours), because peptides generated by proteolytic breakdown of the antigen can enter the appropriate processing pathway, leading to presentation in association with class I molecules on the cell membrane. However, in general, pre-formed soluble antigen does not reach this processing and presentation pathway, and does not elicit class I restricted CTL. Therefore conventional non-living vaccines, while eliciting antibody and T helper responses, do not generally induce CTL-mediated Immunity. The combination of the two adjuvants QS21 and 3D-MPL can overcome this serious limitation of vaccines based on recombinant proteins, and induce a wider spectrum of immune responses.

CTLS specific for CS protein have been shown to protect from malaria in mouse model systems (Romero et al. Nature 341:323 (1989)). In human trials where volunteers were immunised using irradiated sporozoites of *P. falciparum*, and shown to be protected against subsequent malaria challenge, induction of CTL specific for CS epitopes was demonstrated Malik et al. Proc. Natl. Acad. Sci. U.S.A. 88:3300 (1991))..

The ability to induce CTLs specific for an antigen administered as a recombinant molecule is relevant to malaia vaccine development, since the use of irradiated sporozoites would be impractical, on the grounds of production and the nature of the immune response.

In addition to malaria vaccines, the ability to induce CTL responses would benefit vaccines against herpes simplex virus, cytomegalovirus, human Immunodeficiency virus, and generally all cases where the pathogen has an intracellular life stage.

Likewise, CTL specific for known tumour antigens could be induced by a combination of a recombinant tumour antigen and the two adjuvants. This would allow the development of anti cancer vaccines.

In certain systems, the combination of 3D-MPL and QS21 have been able to synergistically enhance interferon γ production. The present inventors have demonstrated the synergistic potential of 3D-MPL and QS21 by utilising a herpes simplex antigen known as gD$_2$t. gD$_2$t is a soluble truncated glycoprotein D from HSV-2 and is produced in CHO cells according to the methodology Berman et al. Science 222 524–527(1983).

IFN-γ secretion is associated with protective responses against intracellular pathogens, including parasites, bacteria and viruses. Activation of macrophages by IFN-γ enhances intracellular killing of microbes and increases expression of Fc receptors. Direct cytotoxicity may also occur, especially in synergism with lymphotoxin (another product of TH1 cells). IFN-γ is also both an inducer and a product of NK cells, which are major innate effectors of protection. TH1 type responses, either through IFN-γ or other mechanisms, provide preferential help for IgG2a immunoglobulin isotypes.

Glycoprotein D is located on the viral envelope, and is also found in the cytoplasm of infected cells (Eisenberg R. J. et al J. of Virol. 1980 35 428–435). It comprises 393 amino acids including a signal peptide and has a molecular weight of approximately 60 kD. Of all the HSV envelope glycoproteins it is probably the best characterized (Cohen et al. J. Virology 60 157–166). It is known to play a central role in viral attachment to cell membranes in vivo. Moreover, glycoprotein D has been shown to be able to elicit neutralizing antibodies in vivo (Eing et al. J. Med Virology 127: 59–65). However, latent HSV-2 virus can still be reactivated and induce recurrence of the disease despite the presence of high neutralizing antibody titre in the patients' sera. It is therefore apparent that the ability to induce neutralizing antibody alone is insufficient to adequately control the disease.

In order to prevent recurrence of the disease, any vaccine will need to stimulate not only neutralizing antibody, but also cellular immunity mediated through T-cells, particularly cytotoxic T-cells.

In this instance the gD$_2$t is HSV2 glycoprotein D of 308 amino acids which comprises amino acids 1 though 306 of the naturally occurring glycoprotein with the addition of Asparagine and Glutamine at the C terminal end of the truncated protein. This form of the protein includes the signal peptide which is cleaved to yield a mature 283 amino acid protein. The production of such a protein in Chinese Hamster ovary cells has been described in Genentech's European patent EP-B-139 417.

The mature truncated glycoprotein D ($rgD_2t$) or equivalent proteins secreted from mammalian cells, is preferably used in the vaccine formulations of the present invention.

The formulations of the present invention are very effective in inducing protective immunity in a genital herpes model in guinea pigs. Even with very low doses of antigen (e.g. as low as 5 µg $rgD_2t$) the formulations protect guinea pigs against primary infection and also stimulate specific neutralising antibody responses. The inventors, utilising formulation of the present invention, have also demonstrated Effector cell mediated responses of the TH1 type in mice.

Accordingly, the present invention provides a vaccine or pharmaceutical formulation comprising an antigen in conjunction with 3 Deacylated monophosphoryl lipid A and QS21. Such a formulation is suitable for a broad range of monovalent or polyvalent vaccines.

Preferably the vaccine formulations will contain an antigen or antigenic composition capable of eliciting an immune response against a human or animal pathogen, which antigen or antigenic composition is derived from HIV-1, (such as gp120 or gp160), any Feline Immunodeficiency virus, human or animal herpes viruses, such as gD or derivatives thereof or Immediate Early protein such as ICP27 from HSV-1 or HSV-2, cytomegalovirus (esp Human, such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus and hepatitis E virus, or from other viral pathogens, such as Respiratory Syncytial virus, human papilloma virus or Influenza virus, or derived from bacterial pathogens such as Salmonella, Neisseria, Borrelia (for example OspA or OspB or derivatives thereof), or Chlamydia, or Bordetella for example P.69, PT and FHA, or derived from parasites such as plasmodium or Toxoplasma.

The formulations may also contain an anti-tumour antigen and be useful for immunotherapeutically treating cancers.

The formulation may also be useful for utilising with herpetic light particles such as described in International Patent Application No. PCT/GB92/00824 and, International Patent Application No. PCT/GB92/00179.

Derivatives of Hepatitis B Surface antigen are well known in the art and include, inter alia, those $PreS_1$, $PreS_2$ S antigens set forth described in European Patent applications EP-A-414 374; EP-A-0304 578, and EP 198-474.

In a further aspect of the present invention there is provided a vaccine as herein described for use in medicine.

The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL: QS21. Typically for human administration QS21 and 3-D MPL will be present in a vaccine in the range 1 µg–100 µg, preferably 10 µg–50 µg per dose. Often the vaccine will not require any specific carrier and be formulated in an aqueous or other pharmaceutically acceptable buffer. In some cases it may be advantageous that the vaccines of the present invention will further contain alum or be presented in an oil in water emulsion, or other suitable vehicle, such as for example, liposomes, microspheres or encapsulated antigen particles.

Vaccine preparation is generally described in New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1–1000 µg of protein, preferably 2–100 µg, most preferably 4–40 µg. An optimal amount for a particular vaccine can be ascertained by standard studies involving observation of appropriate immune responses in subjects. Following an initial vaccination, subjects may receive one or several booster immunisation adequately spaced.

The formulations of the present invention maybe used for both prophylatic and therapeutic purposes.

Accordingly in one aspect, the invention provides a method of treatment comprising administering an effective amount of a vaccine of the present invention to a patient.

EXAMPLES
1.0 Synergy between 3D-MPL and QS21 for induction of Interferon γ secretion.

In order to test the ability of 3D-MPL and QS21 based adjuvant formulations of $rgD_2t$, to induce effector cell mediated immune responses, groups of Balb/c mice were vaccinated, and their draining lymph node cells tested for IFN-γ secretion as described below.
1.1 rgD2t formulations This experiment compared three adjuvant formulations:

i) $rgD_2t$ in 3D-MPL ii) $rgD_2t$ in QS21 iii) $rgD_2t$ in 3D-MPL/QS21

These formulations were made up as follows. $rgD_2t$ was produced in CHO cells and corresponds to the mature 1–283 amino acids of HSV-2 gD and is produced according to the methodology of Berman (supra) and EP 0139417.

*$rgD_2t$/3D-MPL

5 µg of $rgD_2t$/dose are incubated 1 h, under agitation, at room temperature, then mixed with a 3D-MPL suspension (25 µg/dose). The volume is adjusted to 70 µl/dose using a sodium chloride solution (5M, pH 6.5±0.5) and water for injection to obtain a final concentration of 0.15M sodium chloride. pH is kept at 6.5±0.5.

*$rgD_2t$/QS21

5 µg $rgD_2t$/dose are incubated 1 h at room temperature under agitation The volume is adjusted using sodium chloride solution (5M, pH 6.5±0.5) and water for injection to 70 µl. QS21 (10 µg/dose) is then added. pH is kept at 6.5±0.5.and sodium chloride final concentration at 0.15M.

* $rgD_2t$/3D-MPL/QS21.

5 µg $rgD_2t$/dose are incubated 1 h at room temperature under agitation. 3D-MPL (25 µl/dose) is added as an aqueous suspension. The final volume of 70 µl is completed by addition of an aqueous solution of QS21 (10 µg/dose) and the pH kept at 6.5±0.5 and the sodium chloride concentration at 0.15M.
1.2 IMMUNISATION Mice were injected into the hind footpads with 35 µL/footpad of formulation. Thus each mouse received 70 µL. Immunisation were on days 0, and 14. Animals were sacrificed on day 21.

1.3 INTERFERON γ ASSAYS

Popliteal lymph node cells from immunised mice were stimulated in vitro using $rgD_2t$ at 10, 1, 0.1, 0 µg/ml. Triplicate cultures (200 µl volumes) were set up in round bottom 96-well microtiter plates, using $2×10^5$ responder cells and $2×10^5$ irradiated (3000 rad) syngeneic naive spleen cells. Culture medium was RPMI 1640 with 10% foetal calf serum. Aliquots of 100 µl of culture medium from each replicate were harvested and pooled for IFN-γ determinations. Cultures were assayed at 72 hours. For all assays, a control group using ConA (Boehringer Mannheim) at 5 µg/mL was included. This was always positive.

Secretion of IFN-γ was determined using a commercial ELISA assay manufactured by Holland Biotechnology (distributed by Gibco). Assays were carried out on 100 µl of pooled supernatant from triplicate wells.

Secretion of IFN-γ above the assay background of 50 pg/µl was observed in all three formulation groups (see Table). In addition, a synergistic effect between QS21 and 3D-MPL was observed. While each adjuvant on its own induced cells capable of secreting IFN-γ in response to $rgD_2t$, their combination induced more than twice the sum of individual responses.

1.4 Results

Synergy between QS21 and 3D-MPL for induction of IFN-γ secretion.

| Immunization: | | QS21/3D-MPL rgD2t | QS21 rgD2t | 3D-MPL rgD2t |
|---|---|---|---|---|
| In vitro | 10.0 | 1351 | 1105 | 515 |
| stimulation | 1.0 | 914 | 116 | 192 |
| (µg/mL gD2t): | 0.1 | 335 | <50 | 143 |
| | 0.0 | 101 | <50 | 139 |

IFN-γ is expressed in pg/mL.

The table clearly shows that the combined vaccine induces IFN-γ-secretion in a synergistic manner.

2.0 Synergy Between 3D-MPL and QS21 for the induction of CTLs

In order to test the ability of RTS,S particles in 3D-MPL and QS21 based adjuvant formulations to induce CTLs, groups of B10 .BR mice were immunised and their spleen cells stimulated in vitro and tested in cytotoxicity assays on L cells expressing the CS protein.

2.1 Formulation of RTS,S particles.

RTS,S particles were formulated in three different compositions:

1. RTS,S particles ((10µg) with QS21 (10µg) and 3D-MPL (254µg);
2. RTS,S particles ((10µg) with QS21 (10µg);
3. RTS,S particles ((10µg) with 3D-MPL (25µg);

The formulations were made up as follows:

RTS, S/3 D-MPL

10 µg of RTS,S particles/dose was incubated at room temperature under agitation then mixed with a 3D MPL aqueous suspension (25 µg/dose). The volume is then adjusted to 70 µl/dose using water for injections and a sodium chloride solution (5N, pH 6.5±0.5) to reach a final concentration of 0.15M sodium chloride (pH is kept at 6.5±0.5).

RTS,S/QS21

10 µg of RTS,S particles/dose incubated 1 h. at room temperature under agitation. The volume is adjusted using water for injection and a sodium chloride solution (5N, pH 6.5±05) and completed to a final volume of 70 µl/dose with an aqueous solution of QS21 (10µg/dose). pH is kept at 6.5±0.5 and sodium chloride final concentration at 0.15M.

RTS,S /3D-MPL/QS21

10 µg of RTS,S particles/dose are incubated 1 h. at room teperature under agitation then mixed with a 3D-MPL (aqueous suspension (25 µg/dose) The volume is then adjusted with water for injection and a sodium chloride solution (5D pH 6.5±0.5). The final volume is completed by addition of an aqueous solution of QS21 (10µg/dose). pH is kept at 6.5±0.5, and sodium chloride final concentration at 0.15 M.

2.2 Immunisation of mice with RTS,S particles

Four to six week old female mice of the strain B10.BR ($H-2^k$) were purchased from IFFA CREDO (France). Groups of 3 animals were immunised by intra foot-pad injection of 35 µL of antigen formulation into each hind limb. The animals were boosted with a second equal dose of antigen injected two weeks later.

2.3. In vitro stimulation on anti CS CTL

Two weeks after the boost, spleen cells were harvested and stimulated in vitro using syngeneic fibroblasts transfected with the *P. falciparum* circumsporozoite protein gene (7G8 clone). These CS-transfectant cells have been described in the paper by Kumar, S. et al. (1988), Nature 334:258–260.

The cultures were established in RPMI 1640 medium supplemented with 10% of heat inactivated foetal calf serum and usual additives, in conditions well known to those of skill in the art.

Responder cells were cultured at a concentration of $10^6$ cells/mL in the presence of $10^5$ CS-transfectants per mL. To prevent proliferation of CS-transfectant cells, these were irradiated using a dose of $2×10^4$ rad. The cultures were fed by replacing ½ of culture medium on day 3 and 6, and tested for cytolytic activity on day 7.

2.4. Cytotoxicity assay for anti-CS CTL

Responder cell cultures were harvested, washed, and mixed at ratios varying from 100:1 to 0.3:1 with a constant number of 2000 target cells, in volumes of 200 µL of medium in V-bottom 96-well plates. Target cells were syngeneic fibroblast cells that had been labelled with $^{51}Cr$.

Two different types of target cells were used:

1. L cells
2. CS transfected L cells

These are described in: Kumar, S. et al. (1988), Nature 334:258–260.

The assay was incubated for 6 hours at 37° C., then the amount of radioactivity released into the supernatant by lysis of target cells was determined. Cytolytic activity is expressed as % specific lysis:

Results:

| | | % Specific lysis by formulation: | | |
|---|---|---|---|---|
| Target cells: | Effector: target ratio | 1. RTS,S/ QS21/ 3D-MPL | 2. RTS,S/ QS21/ | 3. RTS,S/ 3D-MPL |
| CS transfected L cells | 100 | 58 | 17 | 1 |
| | 30 | 53 | 10 | 0 |
| | 10 | 47 | 5 | 1 |
| | 3 | 27 | 1 | 0 |
| | 1 | 11 | 0 | 0 |
| | 0.3 | 2 | -2 | -1 |
| L cell | 100 | 3 | -2 | 5 |
| | 30 | -2 | 1 | 4 |
| | 10 | 0 | -1 | 2 |
| | 3 | 0 | 3 | 4 |
| | 1 | -1 | 4 | 2 |
| | 0.3 | 3 | 1 | 2 |

Immunisation of B10.BR mice with RTS,S adjuvanted with QS21 and 3D-MPL (formulation #1) induced in the spleen high levels of CTL specific for the circumsporozoite component of RTS.S. Immunisation with RTS.S particles adjuvanted with QS21 (formulation #2) also induced CTL in the spleen, but only at about 1/30 th of the levels given by formulation #1. RTS.S with 3D-MPL (formulation #3) did not induce CTL.

Since the target cells used in this assay do not express MHC class II molecules, the effector cells can be assumed to be $CD8^+$, class I restricted CTL.

3. Other formulation

Hepatitis B Surface Antigen, Alum 3D-MPL and QS21.

The preparation B Surface antigen (HBsAg) is well documented. See for example Harford et al Develop. Biol. Standard 54 p125 (1983), Gregg et al Biotechnology 5 p479 (1987) EP-A-O 226 846 and EP-A-299 108 and references therein. 3D-MPL was obtained from Ribi Immunochem. QS21 was obtained from Cambridge Biotech, and Aluminium hydroxide was obtained from Superfos (Alhydrogel).

A number of different formulations were made up for studies of cell mediated immunity in mice and for studies in Rhesus monkeys.

3.1 Formulation 1 was made up in phosphate buffer (pH 6.8) to comprise the following per 60 µl dose.

| | |
|---|---|
| 20 µg | HBsAg |
| 30 µg | $Al(OH)_3$ |
| 30 µg | 3D-MPL |
| 10 µg | QS21 |
| 10 mM | $PO_4^{3-}$ |
| 0.15M | NaCl |

The formulation was made up in the following manner. 20ptg HBsAg/dose was incubated with $Al(OH)_3$ for one hour at room temperature with gentle shaking. 3D-MPL was added as an aqueous suspension, and the formulation completed by the addition of QS21, phosphate buffer and sodium chloride and incubated for one hour at room temperature. The final formulation had a pH of between 6.5 and 7.0 and used for foot pad studies in mice.

3.2 Formulation 2 was made up in a phosphate buffer (pH6.8) to comprise the following per 200 µl dose.

| | |
|---|---|
| 1 µg | HBsAg |
| 100 µg | $Al(OH)_3$ |
| 50 µg | 3D-MPL |
| 20 µg | QS21 |
| 10 mM | $PO_4^{3-}$ |
| 0.15M | NaCl |

The formulation was made up in the following manner. HBsAg and $Al(OH)_3$ were incubated together for one hour at room temperature with gentle shaking. The formulation was completed by the addition of $Al(OH)_3$, 3D-MPL as an aqueous suspension and QS21, with phosphate buffer and sodium chloride solution and incubated again for thirty minutes. The pH of the formulation was kept between 6.5 and 7.0 and used for humoral immunity studies in mice.

3.3 Formulation 3 was made up in a similar manner, in a phosphate buffer (pH6.5–7.0) to contain the following per 1 ml dose:

| | |
|---|---|
| 10 µg | HBsAg |
| 500 µg | $Al(OH)_3$ |
| 50 µg | 3D-MPL |
| 10 µg | QS21 |

The formulation was used for monkey studies.

4. Conclusions

The combination of the two adjuvants QS21 and 3D-MPL with the recombinant particulate antigen RTS.S resulted in a powerful induction of CS protein specific CTL in the spleen. QS21 enhances induction of CTL on its own, while 3D-MPL does not. The combination can be said to act in a synergistic way, because it has an effect that is larger than the sum of the separate effects of each adjuvant. The synergy between these two adjuvants for CTL induction is a surprising observation which supports our observation of synergy between QS21 and 3D-MPL for induction of T cells capable of secreting IFN-γ in response to stimulation with the soluble recombinant protein $rgD_2t$. This finding has important implications for the use of recombinant molecules as vaccines for induction of CTL mediated immunity, since the combination of the two adjuvants QS21 and 3D-MPL can overcome this serious limitation of vaccines based on recombinant proteins, and induce a wider spectrum of immune responses than hitherto.

The mouse cell mediated immunogenicity data show that QS21 based formulations of $rgD_2t$ induce a significant synergistic TH 1 type T cell response (IFN-γ secretion). Such TH1 type T cells have been shown to be involved in induction of delayed type hypersensitivity responses in mice. Our own data in prophylaxis of HSV disease show that concomitant induction of neutralizing antibody titers and antigen specific DTH responses affords the best protection against herpes simplex disease.

Taken together, these data suggested that QS21 formulations of $rgD_2t$ may be effective in inducing a protective response against HSV disease. The data presented show an unexpected synergistic effect between 3D Monophosphoryl lipid A and QS21, in inducing IFN-γ secreting antigen specific T cells. Such a synergy may translate in improved ability to induce a protective response against HSV disease, and indeed these formulations are effective in protecting against disease in guinea pigs.

We claim:

1. A vaccine composition comprising:
   (a) an antigen;
   (b) QS21; and
   (c) 3-De-O-acylated monophosphoryl lipid A (3D-MPL).

2. A vaccine as claimed in claim 1 wherein the ratio of QS21:3D-MPL is from 1:10 to 10:1.

3. A vaccine composition as claimed in claim 1 capable of invoking a cytolytic T cell response in a mammal to the antigen.

4. A vaccine composition as claimed in claim 1 capable of stimulating interferon γ production.

5. A vaccine composition as claimed in claim 2 wherein the ratio of QS21:3D-MPL is from 1:1 to 1:2.5.

6. A vaccine as claimed in claim 1 wherein the antigen is a tumour antigen.

7. A method of treating a mammal suffering from or susceptible to a pathogenic infection comprising the administration of a safe and effective amount of a composition according to claim 1.

8. A method of treating a mammal suffering from cancer comprising the administration of a safe and effective amount of a composition according to claim 1.

9. A process for making a vaccine composition according to claim 1 comprising admixing QS21 and 3D-MPL with an antigen.

10. A vaccine composition as claimed in claim 1 comprising an antigen derived from the group consisting of Herpes Simplex Virus type 1, Herpes Simplex virus type 2, Human cytomegalovirus, Hepatitis A, B, C or E, Respiratory Syncytial virus, human papilloma virus, Influenza virus, Salmonella, Neisseria, Borrelia, Chlamydia, Bordetella, Plasmodium and Toxoplasma.

11. A pharmaceutical composition useful for adjuvanting an immune response comprising an adjuvanting effective combination of QS21 and 3-De-O-acylated monophosphoryl lipid A (3D-MPL).

12. The composition as claimed in claim 11 capable of invoking a cytolytic T cell response in a mammal to an antigen.

13. The composition as claimed in claim 11 capable of stimulating interferon γ production.

14. A method for stimulating a cytotoxic T cell response in an animal comprising introducing into said animal a cytotoxic T cell response stimulating amount of the composition of claim 1.

15. A method for stimulating a γ-interferon response in an animal comprising introducing into said animal a γ-interferon response stimulating amount of the composition of claim 1.

16. The vaccine composition of claim 1 wherein the QS21 and the 3D-MPL synergistically enhance the immune response in an animal to the antigen.

17. The composition of claim 11 in which the QS21 and 3D-MPL synergistically enhance the immune response in an animal to an antigen.

18. A method of enhancing the immune response in an animal to an antigen which comprises administering to the animal (a) the antigen, (b) QS21, and (c) 3D-MPL.

19. The method of claim 18 in which the animal is a human.

20. The method of claim 18 wherein the QS21 and the 3D-MPL are administered at a ratio of QS21:3D-MPL of from 1:10 to 10:1.

21. The method of claim 18 wherein the ratio of QS21:3D-MPL is from 1:1 to 1:2.5.

22. The method of claim 18 wherein the antigen is derived from any of Herpes Simplex Virus type 1, Herpes Simplex virus type 2, Human cytomegalovirus, Hepatitis A, B, C or E, Respiratory Syncytial virus, human papilloma virus, Influenza virus, Salmonella, Neisseria, Borrelia, Chlamydia, Bordetella, Placsniodium, and Toxoplasma.

23. The method of claim 18 wherein the antigen is a tumor antigen.

24. The method of claim 18 wherein a cytolytic T cell response to the antigen is induced.

25. The method of claim 18 wherein interferon γ production is stimulated.

26. The method of claim 18 wherein the QS21 and 3D-MPL synergistically enhance the immune response.

* * * * *